United States Patent [19]
Spivey et al.

[11] Patent Number: 5,305,752
[45] Date of Patent: Apr. 26, 1994

[54] ACOUSTIC IMAGING DEVICE

[75] Inventors: Brett A. Spivey; Peter J. Martin, both of Encinitas; Douglas A. Palmer, San Diego, all of Calif.

[73] Assignee: Thermotrex Corporation, San Diego, Calif.

[21] Appl. No.: 891,851

[22] Filed: Jun. 1, 1992

Related U.S. Application Data

[63] Continuation-in-part of Ser. No. 708,354, May 31, 1991, abandoned.

[51] Int. Cl.$^5$ .............................................. A61B 8/00
[52] U.S. Cl. .................................. 128/661.02; 73/602
[58] Field of Search ...................... 128/660.01, 660.06, 128/660.07, 661.02, 915, 916; 73/602; 364/413.2, 413.21, 413.25

[56] References Cited

U.S. PATENT DOCUMENTS

| | | | |
|---|---|---|---|
| 4,594,662 | 6/1986 | De Vaney | 128/916 X |
| 4,598,366 | 7/1986 | De Vaney | 128/916 X |

OTHER PUBLICATIONS

Kah, A. "Computerized Tomography W/X-Ray, Emission & UTS Sources", Proc. IEEE v. 67 #9 Sep. 1979 pp. 1245-1272.

Primary Examiner—Francis Jaworski
Attorney, Agent, or Firm—John R. Ross

[57] ABSTRACT

An acoustic imaging device is disclosed which utilizes mathematical inversion of scattered acoustic wave information to produce an image. A preferred embodiment of the device consists of a ring of acoustic transducers which encircle a medium to be imaged. The medium is sequentially insonified by each transducer with subsequent reception of the scattered waves by the remaining transducers. Explicit mathematical inversion of the scattered wave data using a remap algorithm results in a two-dimensional map of the scattering potential of the medium. Sound speed and density maps can be obtained from a map of the scattering potential. This device is utilizable for imaging of human tissue in vivo and in vitro, and for nondestructive evaluation of materials.

15 Claims, 12 Drawing Sheets

| PREPROCESSING | |
|---|---|
| STEP | OPERATION |
| 1. | Repair dead channels in signal and background by averaging with adjacent channels. |
| 2. | Subtract systematics/switch noise data. |
| 3. | Zero center diagonals to eliminate transmitter/receiver cross-talk. |
| 4. | Calibrate gains of receivers and transmitters by averaging in background. Result is gain matrix. |
| 5. | Normalize signal and background using gain matrix. |
| 6. | Select one of the following techniques: |
| (Optional) | Direct (Palmer method):<br>Feed signal directly to reconstructor which results in transmitters being imaged as "scatterers". |
| (Optional) | *Subtracted:* (Born)<br>Subtract background from signal. Feed signal to reconstructor. |
| (Optional) | *Warping:* Divide signal by background, low pass filter and multiply by signal. Feed to reconstructor. |
| (Optional) | *Rytov:* Divide signal by background. Take log and multiply by signal. Feed to reconstructor. |

FIG. 7

ACOUSTIC IMAGING DEVICE

This application is a continuation in-part of Ser. No. 07/708,354 filed May 31, 1991 and now abandoned.

BACKGROUND OF THE INVENTION

This invention relates to imaging systems and methods and in particular to systems and methods for reconstructing acoustic properties of an object using mathematical procedures and acoustic wave data.

In conventional parallel beam transmission tomography, such as utilized in x-ray computed tomography (x-ray CT), for example, the attenuation of a narrow beam of x-rays is measured as this beam probes an inhomogenous medium along many different trajectories. The information contained in these attenuation projections is then used to reconstruct a tomographic image of the medium. The success of x-ray CT (manifested in the resolution and clarity of the images) is fundamentally linked to the very short wavelength of the incident x-ray beam ($°1$ Å). The scattering effects, in the form of diffraction, refraction, and reflection, of the incident x-ray beam are negligible and the dominating attenuation mechanism is absorption. The lack of diffraction effects in x-ray CT results in quite simplified mathematical reconstruction techniques which are used to produce a quality tomographic image. A review of x-ray CT methods is given in, for example, A. J. Devaney, "A Filtered Backpropagation Algorithm for Diffraction Tomography", Ultrasonic Imaging 4, 336–350 (1982); and R. Mueller et. al., "Reconstructive Tomography and Applications to Ultrasonics", Proc. IEEE 67, 567–587 (1979).

In ultrasonic tomography, the acoustic wavelengths are much longer ($\approx 1$ mm) and the diffraction effects of the incident acoustic beam by the medium are not negligible. In this case, the attenuation of a sound wave is substantially affected by scattering effects such as diffraction, refraction, and reflection, as well as absorption. The simplified mathematical reconstruction algorithms used in conventional x-ray CT, which tacitly assume that attenuation is due to absorption, are not applicable in this case.

Ultrasonic Diffraction Tomography (UDT) techniques attempt to mathematically reconstruct a tomographic image of a medium from scattered acoustic wave data with full consideration to the scattering effects associated with the much longer acoustic wavelengths involved. This is done by considering the full wave equation with diffraction effects, a much more difficult problem to develop and implement than the geometrical wave approximation used in x-ray CT. UDT techniques attempt to determine the internal structure of an object which is semi-transparent to acoustic waves from a partial or complete set of scattered wave data interrogated at the boundary of the object. A number of these inverse scattering solutions have been theoretically considered, from simplified algorithms which use the Born approximation (E. Wolf, "Three-dimensional Structure Determination of Semi-Transparent Objects from Holographic Data", Opt. Comm. 153–156 (1969)) and Rytov approximations (A. J. Devaney, "Inverse Scattering Within the Rytov Approximation", Opt. Lett. 6,374 (1981)) to computer intensive full-wave reconstruction algorithms (S. Johnson and M. Tracy, "Inverse Scattering Solutions by a Sinc Basis, Multiple Source, Moment Method", Ultrasonic Imaging 5, 361–375 (1983) and references therein).

Prior art patents included Devaney (U.S. Pat. No. 4,598,366) and Johnson (U.S. Pat. No. 4,662,222). The patents of Johnson claim iterative algorithms which form an initial sound speed estimate, calculate the measurement which would be expected from that estimate, and then update the estimate. This process is repeated until a residual error parameter is small enough. The patents of Devaney form an image directly from the data using Born and Rytov inversions with a technique called filtered backpropagation. These prior acoustic methods lack efficiency and therefore require a great amount of computation.

It is therefore an object of this invention to provide a system and method which will efficiently reconstruct an image based on the density and/or the sound speed of a medium.

SUMMARY OF THE INVENTION

This invention provides an acoustic imaging device which utilizes scattered acoustic wave information to produce an image. The system consists of a ring of acoustic transducers which at least partially encircle a medium to be imaged. Explicit mathematical inversion of the scattered wave data using a remap algorithm results in a two-dimensional map of the complex scattering potential of the medium. Sound speed and density maps can be obtained from a map of the complex scattering potential. This device can be utilized for imaging of human tissue in vivo and in vitro, and for nondestructive evaluation of materials. A preferred embodiment of the device consists of a ring of acoustic transducers which encircle a medium to be imaged. The medium is sequentially insonified by each transducer with subsequent reception of the scattered waves by the remaining transducers.

BRIEF DESCRIPTION OF THE DRAWINGS

FIG. 7 is a listing of preprocessing step.

DETAILED DESCRIPTION OF PREFERRED EMBODIMENTS

Concept

The density and sound speed within a medium uniquely defines a mathematical term called the "complex scattering potential" of the medium. When an acoustic wave is transmitted through a medium which has a spatially varying density and sound speed, this medium scatters acoustic waves in all directions. The phase and amplitude of the scattered acoustic waves emitted from the medium contains information defining the Fourier transform of the scattering potential of the medium.

This invention provides a system for insonifying a medium with a single frequency acoustic wave from a plurality of directions, and for measuring the amplitude and phase of acoustic waves scattered into a plurality of directions from the medium. The Fourier transform of the complex scattering potential is determined from this amplitude and phase data, and an inverse Fourier transform yields the complex scattering potential of the medium. An efficient mathematical algorithm for determining the complex scattering potential of the medium from the set of scattered acoustic wave information is provided. A preferred embodiment of the invention measures a sufficient set of scattered acoustic waves such that a two-dimensional map of the scattering potential can be determined. This two-dimensional map can be viewed as a thin slice of the density structure of the medium. Sequential imaging of a stack of slices allows one to obtain a three-dimensional image of the medium, as is done, for example, in x-ray computer assisted tomography.

Figure 1:
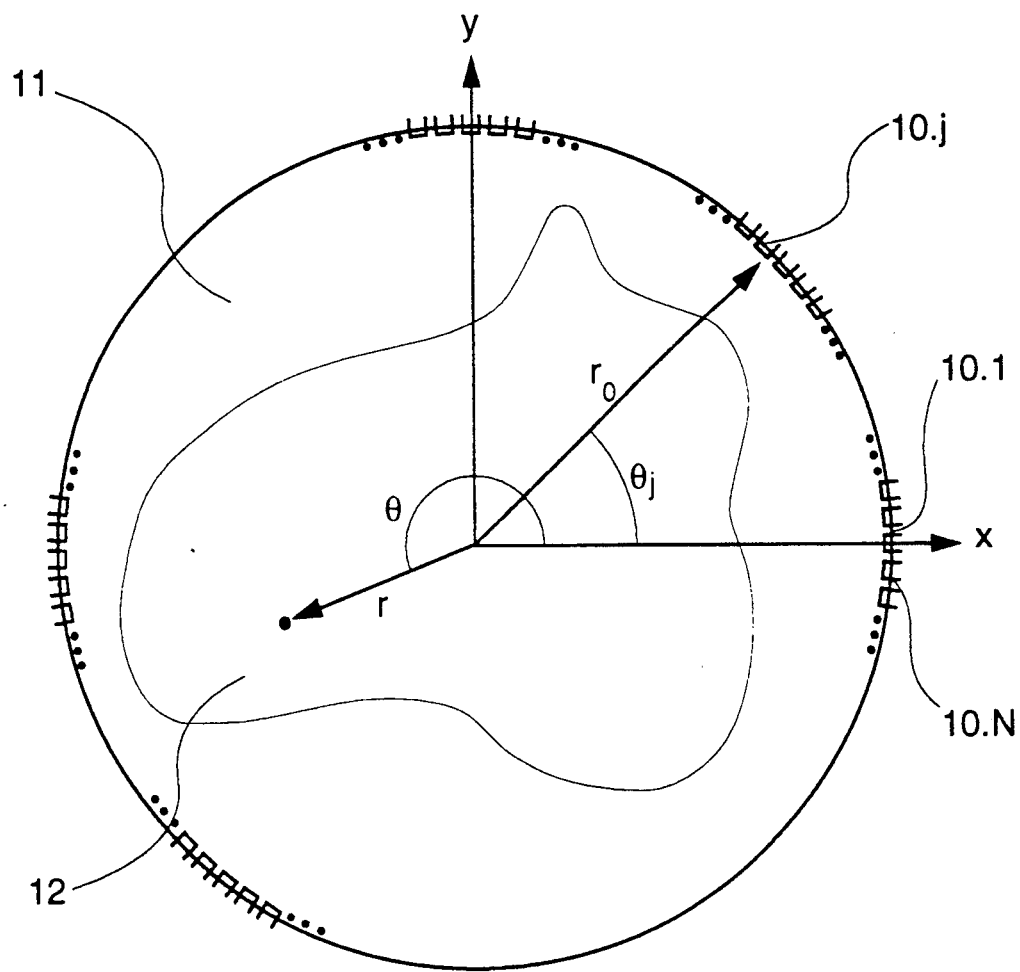
FIG. 1 is a schematic diagram of the cross section of the invention for use in illustrating the mathematical reconstruction algorithm.

A schematic diagram of the cross section of a portion of a preferred embodiment is shown in FIG. 1. In this embodiment, there are N=256 acoustic transducers 10.1, ..., 10.N evenly arranged on the locus of a circle of radius $r_o=51$ mm. The transducers 10, each which can act as either a transmitter or a receiver of acoustic waves, are located in the r, $\theta$ (or x,y) plane. The z-direction is perpendicular to this plane. The transducers circumscribe the medium 12 which is semi-transparent to the acoustic waves. In this preferred embodiment, a fluid resides in the remaining volume 11 to effectively couple acoustic waves between the transducers 10 and the medium 12. (Water is a preferred fluid for imaging human tissue. When imaging other objects a fluid should be chosen which preferably has a density $\rho_o$ and sound speed $c_o$ which are approximately equal to the average density and sound speed of the medium 12.)

This embodiment involves the systematic insonification of the medium by having each transducer 10.$j$ ($j=1, ..., N$) sequentially perform as transmitter of acoustic energy. The phase and amplitude of the scattered acoustic waves due to insonification by transducer 10.$j$ are measured by the remaining transducers 10.$k$ ($k=1, ..., N; k \neq j$). It will be shown here that this information can be explicitly inverted to yield a two-dimensional map of the scattering potential of the medium 12 from which maps of the density and sound speed can be determined.

The wave equation for the acoustic pressure wave $P(x)\exp(i\omega t)$ propagating with frequency $\omega$ through the medium 12 is given by $$\nabla^2 P(x) + k^2(x)P(x) - \nabla \ln \rho(x) \cdot \nabla P(x) = 0 \quad (1)$$

where $\rho(x)$ is the density distribution of the medium and where the spatially varying wavevector $k(x) = [\omega^2/c^2(x) - i\omega \alpha_{visc.}]^{\frac{1}{2}}$ accounts for the spatially varying sound speed $c(x)$ and includes an acoustic energy loss term $\alpha_{visc.}(x,\omega)$ which accounts for viscous heating of the medium. A transformation $P(x) = f(x)\rho(x)^{\frac{1}{2}}$ results in the Helmholtz equation $$\nabla^2 f(x) + S^2(x) f(x) = 0 \quad (2)$$

where $S(x) = \{k^2(x) - \rho(x)^{\frac{1}{2}} \nabla^2 [1/\rho(x)]^{\frac{1}{2}}\}^{\frac{1}{2}}$ is the complex scattering potential of the medium.

We can now describe the acoustic pressure wave in the medium 12 due to transmission of a single frequency acoustic wave (frequency $\omega$) by transducer 10.$j$ located at position $x_j = (r_o, \theta_j)$. This is accomplished by the addition of a source term $\delta'(r - r_o) \delta(\theta - \theta_j)$ to the right hand side of equation 2, $$\nabla^2 f(x) + S^2(x) f(x) = \delta'(r - r_o) \delta(\theta - \theta_j). \quad (3)$$

In equation 3, $$\delta'(r - r_o) \equiv \frac{d}{dr} \delta(r)|_{r=r_o}$$

describes a transducer which acts as a dipole transmitter and receiver of acoustic waves. The dipole transmitter is given by a coherent sum of two monopole transmitters closely spaced along the radial direction. A dipole transmitter was chosen for this algorithm because it closely approximates the acoustic radiation pattern emitted by the transducers selected for the preferred embodiment. The radiation pattern of any acoustic transducer can be exactly calculated as a weighted sum of monopole, dipole, quadrapole, etc. radiation patterns, as discussed in or example "Classical Electrodynamics", J. D. Jackson, Chap. 16, J. Wiley and Sons, New York, 1962. Therefore, this reconstruction algorithm can be modified to account for different transducer designs. Because we are interested in a two-dimensional reconstruction of $S(x)$, we can suppress the dimension z which extends out of the plane of FIG. 1 and solve equation 3 in the two dimensions $x = (r, \theta) = (x,y)$. Equation 3 can be solved in the Born approximation to give the acoustic pressure wave $P(x_k) = f(x_k)\rho_o^{\frac{1}{2}} \equiv m_{jk}$ at transducer 10.$k$ due to insonification of the medium by transducer 10.$j$, $$m_{jk} = \int a_j(x) a_k(x) S(x) dx \quad (4)$$

where $$\left[ \frac{1}{r} \frac{\partial}{\partial r} r \frac{\partial}{\partial r} + \frac{1}{r^2} \frac{\partial^2}{\partial \theta^2} + k_o^2 \right] a_j(r,\theta) = \quad (5)$$

$$\delta(r - r_o) \delta(\theta - \theta_j) + R \, a_j(\rho,\theta)$$

and $k_o = \omega/c_o$ where $c_o$ is the sound speed of the coupling fluid 11. The Born approximation assumes that the acoustic wave propagates from the transmitter 10.$j$ to a scatterer in the medium and then propagates to receiver 10.$k$ with negligible further interaction with the medium. In equation 5, the source term $R(\theta) \, a_j(\rho, \theta)$ accounts for reflection of acoustic energy from the receiving transducer 10.$j$ back into the medium. The solution to equation 5 is $$a_j(r,\theta) = \sum_{m=-\infty}^{\infty} a_{j,m}(r) \, e^{om\theta} \text{ where} \tag{6}$$

$$a_{j,m}(r) = ke^{-im\theta_j} \frac{H_m'(k_o r_o) \, J_m(k_o r)}{1 - R_m \, J_m(k_o r_o) \, H_m(k_o r_o)} \quad r < r_o.$$

K is a normalization constant, and $\theta_j = 2\pi j/N$. From this point we will use K to signify an arbitrary normalization constant which a person skilled in the art could derive, but has little direct significance for imaging purposes. In equation 6, $J_m(z)$ is the Bessel function of integer order m, $H_m'(z)$ is the first derivative of the Hankel function of integer order m, and $$R(\theta) = \sum_{m=\infty}^{\infty} R_m \, e^{im\theta}.$$

These functions are discussed and tabulated in, for example, "The Pocketbook of Mathematical Functions", by M. Abramowitz and I. Stegun, Chapter 9, pg. 102–153, Verlag Harri Deutsch, 1984. Combining equations 4 and 6 yields $$m_{jk} = K \sum_{p,q=-\infty}^{\infty} \int dx \, C_p(k_o r_o) \, C_q(k_o r_o) \, J_p(k_o r) \, J_q(k_o r) \, e^{ip(\theta-\theta_j)+iq(\theta-\theta_k)} \, S(x) \tag{7}$$

$$\text{where } C_n(k_o r_o) = \frac{H_n'(k_o r_o)}{1 - R_n \, J_n(k_o r_o) \, H_n(k_o r_o)}$$

Equation 7 expresses the measurable coefficients $m_{jk}$ as functions of the unknown scattering potential S (x). It is straightforward to one skilled in the art to mathematically invert equation 7 and to express the scattering potential S (x) as a function of the coefficients $m_{jk}$. This inversion procedure results in $$\tilde{S}\{k_x^{\alpha\beta}, k_y^{\alpha\beta}\} = \tag{8}$$

$$K \sum_{p,q=-N/2}^{N/2} \sum_{j,k=1}^{N} \frac{1}{C_p(k_o r_o) \, C_q(k_o r_o)} \, m_{jk} \, e^{-ip(\theta_\alpha - \theta_j) - iq(\theta_\beta - \theta_k)}$$

where $$\tilde{S}\{k_x^{\alpha\beta}, k_y^{\alpha\beta}\} \equiv \int dx \, e^{ik_x^{\alpha\beta}x + ik_y^{\alpha\beta}y} \, S(x) \tag{9}$$

is the two dimensional Fourier transform of the scattering potential S (x,y) with the arguments $k_x^{\alpha\beta} = -k_o (\sin\theta_\alpha + \sin\theta_\beta)$, $k_y^{\alpha\beta} = k_o (\cos\theta_\alpha + \cos\theta_\beta)$.

We now must solve for S(x) from $\tilde{S}\{k_x^{\alpha\beta}, k_y^{\alpha\beta}\}$. Devaney (U.S. Pat. No. 4,598,366) does this by performing the filtered backpropagation integral:

$$S(\vec{x}) = \frac{k^2}{8\pi^2} \int_{-\pi}^{\pi} d\theta_\alpha \int_{-\pi}^{\pi} d\theta_\beta |\sin(\theta_\alpha - \tag{10}$$

$$\theta_\beta)| \tilde{S}\{k_x^{\alpha\beta}, k_y^{\alpha\beta}\} \, e^{-ik_x^{\alpha\beta}x - ik_y^{\alpha\beta}y}.$$

We believe that our method which we call "remapping" produces a more numerically efficient algorithm. It is performed in the following manner: first we calculate $\tilde{S}\{k_x^{\alpha\beta}, k_y^{\alpha\beta}\}$ for a uniformly spaced array of $\theta_\alpha$, $\theta_\beta$. This allows the sum over p and q in equation 8 to be performed efficiently using a fast Fourier transform algorithm. We believe that a good choice for the spacing of $\Delta\theta = \theta_{\alpha+1} - \theta_\alpha$ to be $\pi/N$ where N is the number of transducers. Next, $\tilde{S}\{k_x^{\alpha\beta}, k_y^{\alpha\beta}\}$ is remapped onto $\tilde{S}\{k_x^\gamma, k_y^\delta\}$ where $k_x^\gamma$ and $k_y^\delta$ are evenly spaced in k, that is, $k_x^{\gamma+1} - k_x^\gamma = \Delta k_x$ and $k_y^{\delta+1} - k_y^\delta = \Delta k_y$ where a good choice for $\Delta k$ is $\Delta k < \pi/r_o$. This remapping is performed by calculating, for each point $(k_x^\gamma, k_y^\delta)$, an interpolated value from the points $(k_x^{\alpha\beta}, k_y^{\alpha\beta})$ which are closest to $(k_x^\gamma, k_y^\delta)$. This remapping allows us to write $$\tilde{S}\{k_x^\gamma, k_y^\delta\} = \int dx \, e^{-ik_x^\gamma x + ik_y^\delta y} \, S(x,y) \tag{11}.$$

The scattering potential S (x,y) can now be calculated efficiently from $\tilde{S}\{k_x^\gamma, k_y^\delta\}$ using a fast Fourier transform algorithm since the points $\tilde{S}\{k_x^\gamma, k_y^\delta\}$ are on a regularly spaced grid. This inversion algorithm is simply $$S(x,y) = K \sum_{\gamma,\delta} \tilde{S}\{k_x^\gamma, k_y^\delta\} \, e^{-ik_x^\gamma x - ik_y^\delta y}.$$

SIMPLIFYING APPROXIMATIONS

We have tested several approximations to simplify the algorithm and to speed up the calculation of our images. These approximations include the Born and Rytov transformations and a transformation which we refer to as the "direct or Palmer" transformation. The Born transformation assumes the measured signal includes the sum of the incident wave $\psi_0$ and the scattered wave $\psi_1$. Thus, when we are using the Born approximative assume that the measured pressure wave $P(x_R)$ represents $\psi_0 + \psi_1$ and we thus subtract $\psi_0$ from the measured pressure wave to obtain $\psi_1$ as representing the scattered wave.

The Rytov transformation assumes a multiplicative relationship between the incident wave and the scattering wave and that the measured wave $P = \psi_0 \exp(\psi_1/\psi_0)$. Thus, to obtain the scattered wave we calculate:

$$\psi_1 = \psi_0 \ln \frac{P}{\psi_0}.$$

Therefore, we divide the measured pressure wave by the background incident wave, take the log and multiply direct or by the incident wave in order to obtain the scattered wave $\psi_1$.

For our preferred Palmer approximation, we assume that essentially all of the measure wave is represented by scattered waves and therefore the measured wave is the scattered wave; or $P = \psi_1$.

Our actual experiments with our prototype device has proven that objects which fill a large portion of the measurement cavity, the Palmer approximation works best. The Born approximation works well to image objects which are very small relative to the size of the cavity. The Rytov approximation works fairly well for objects in between.

It should be noted that, when using the Palmer approximation, the ring of transmitters show up as scatterers, but this is no problem since the ring is outside the object to be imaged.

In order to obtain an image of the medium, we determine $m_{jk}$ which is an $N \times N$ matrix of both the amplitude and phase of the acoustic pressure wave $P(x_k)$ at transducer $10.k$ due to insonification of the medium by transducer $10.j$. This two dimensional matrix is produced by measuring both the amplitude and phase for the waves received by each receiver as produced by each transducer. The calculation of $\bar{S} \{k_1{}^{\alpha\beta}, k_2{}^{\alpha\beta}\}$ in equation 8 then involves a summation of functions which include the measured coefficients $m_{jk}$ and tabulated coefficients $C_p(k_o r_o)$ and $C_q(k_o r_o)$. The summations over p and q can be terminated at values where $C_p(k_o r_o)$ and $C_q(k_o r_o)$ become very large which occurs when $p_{max}, q_{max} > k_o r_o$. This criterion (and the condition that $p_{max}, q_{max} = N/2$) sets the maximum spacing $d_{max}$ allowed between transducers, $d_{max} = 2\pi r_o / N < \lambda_o/2$ where $\lambda_o$ is the average wavelength of the acoustic waves in the medium. Once $\bar{S}(k_1{}^{\alpha\beta}, k_2{}^{\alpha\beta})$ has been determined, it is remapped and an inverse Fourier Transform of it is obtained to produce S (x, y) which is the scattering potential of the medium. S (x, y) is an image of the medium based on scattering potential. By determining S (x, y) at two different frequencies, images based on density $\rho$ (x, y) or sound speed c (x, y) can also be obtained as described below. We have also improved the images by taking independent measurement at many different frequencies and summing the results.

THE DEVICE

Figure 2:
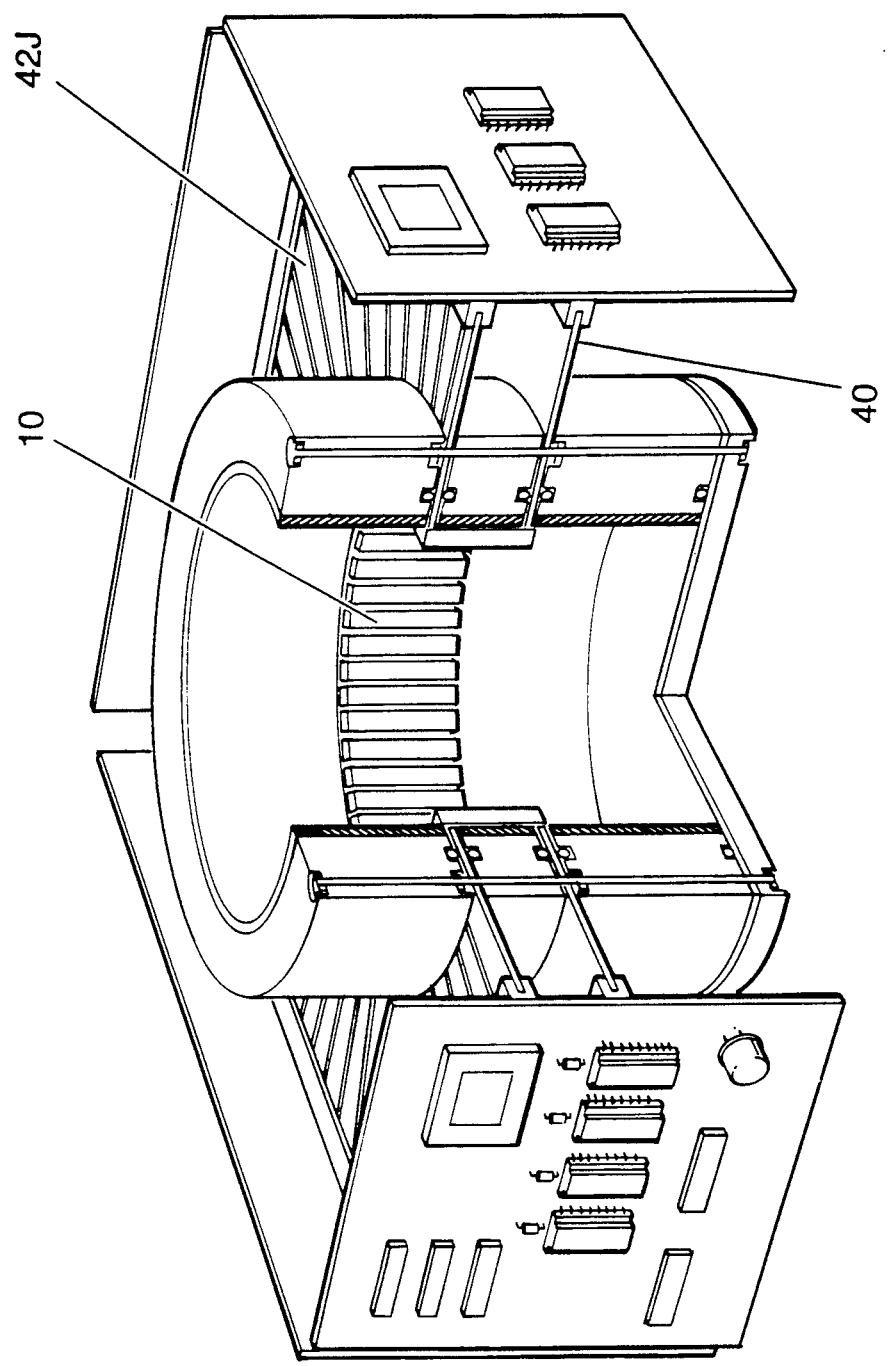
FIG. 2 is illustration of the system of acoustic transducers utilized in this invention.

The transducer portion of a preferred embodiment of the present invention for obtaining two-dimensional images is displayed in FIG. 2. The device consists of $N=256$ acoustic transducers 10 evenly spaced on a circle of radius $r_o=51$ mm. Each acoustic transducer performs at different times as a receiver or a transmitter of acoustic waves. The acoustic frequency is set at 500 kHz which results in a wavelength $\lambda_o=3.0$ mm in water and approximately this wavelength in human tissue. The spacing between transducers is 1.3 mm which is somewhat less than $\lambda_o/2$ as required by the aforementioned conditions. In the preferred embodiment, the acoustic radiation pattern from each transducer is predominantly peaked in the radial (r) dimension which lends itself to the dipole approximation used in the aforementioned derivation of the reconstruction algorithm. The vertical height of the transducers is 25.4 mm, which produces a fairly flat beam of acoustic energy in the z-direction. The thickness of the image slices is roughly equal to the vertical (z) height of the transducers so the image S (x) will comprise an average over the vertical dimension. Alternate embodiments include varying the vertical height to obtain different image slice dimensions.

Figure 3:
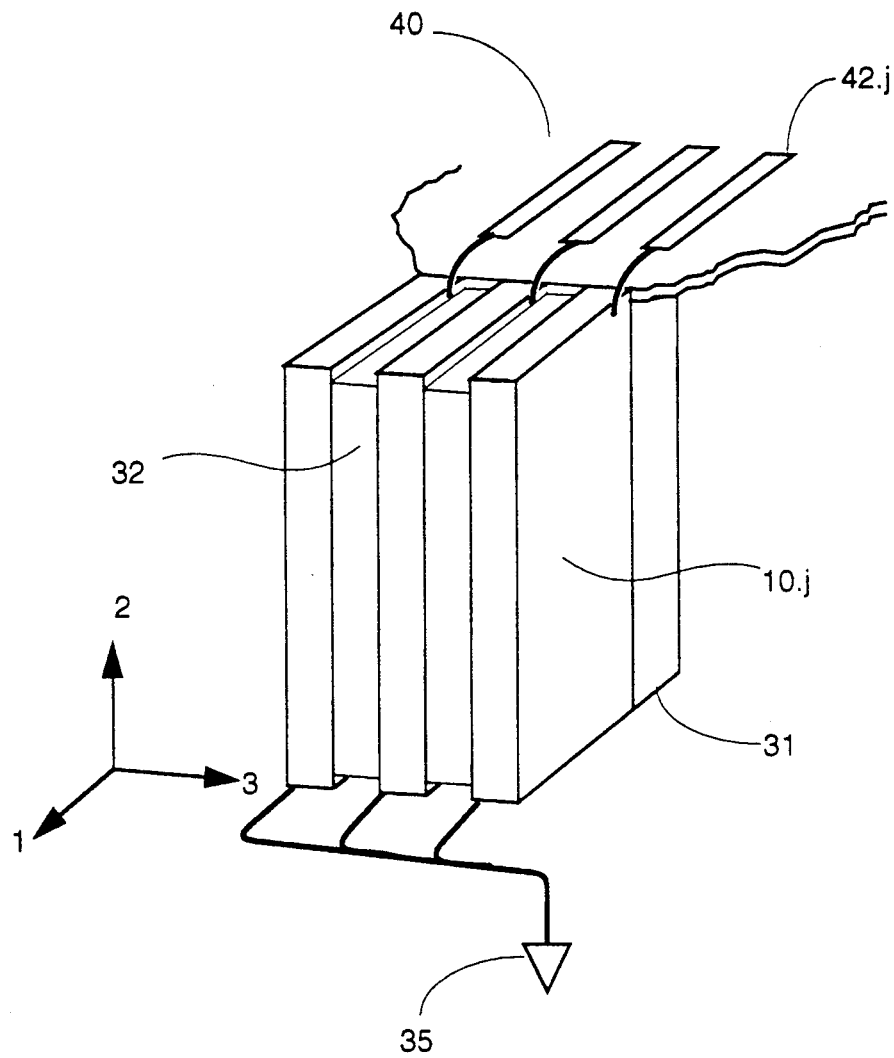
FIG. 3 is a detailed illustration of several of the acoustic transducers.

A detailed illustration of several individual transducers is shown in FIG. 3. Each transducer element $10.j$ ($j=1, \ldots, 256$) is constructed from PZT5A piezoelectric ceramic supplied by Vernitron Piezoelectric Division, Bedford, Ohio. The dimensions of each element are 0.90 mm (3-axis) $\times$ 2.80 mm (1-axis) $\times$ 25.4 mm (2-axis). Electrical energy is supplied along the 3-axis and the 1-axis is dimensioned so that the transducer can resonantly transmit or receive acoustic energy at 500 kHz along the 1-axis. Therefore, the emitted wave diverges cylindrically in (1, 3) plane which is the (x, y) plane shown in FIG. 1 and remains fairly collimated in the vertical (z) direction. Each transducer backing 31 and the spacing between the transducers 32 is comprised of an air-filled silicone foam (Silpak SF-2000) which acoustically and electrically isolates the transducers from each other. FIG. 3 shows that one electrode of each transducer is connected to a common electrical ground 35 and the other electrode of each transducer $10.j$ is connected to an electrical strip line $42.j$ which is etched on a printed circuit board 40. Electrical signals are routed to and from each transducer along these strip lines 42.

ELECTRICAL CIRCUIT

Figure 4:
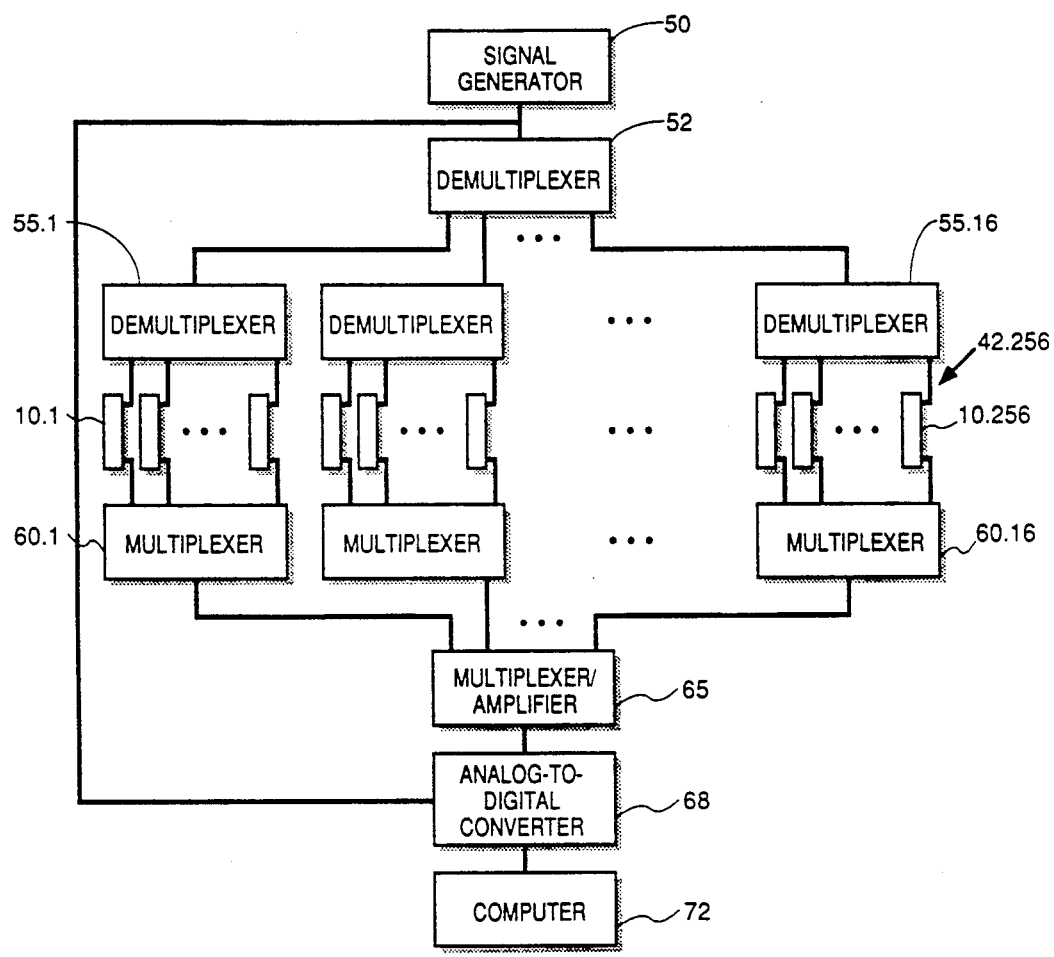
FIG. 4 is block diagram illustrating the electrical circuitry used in the processing of electrical signals from the transducers and the transmission of electrical signals to the transducers.

A block diagram of the electrical processing circuitry is illustrated in FIG. 4. The electrical line from the signal generator/amplifier 50 is split into 16 lines via a 1-to-16 analog demultiplexer 52 and then into 256 lines via 16 1-to-16 analog demultiplexers 55.1, ..., 55.16. Each of these 256 lines are connected to a separate transducer 10.1 to 10.256 through 256 electrical strip lines $42.j$ is shown in FIG. 3. The demultiplexers 52 and 55.1 through 55.16 are programmed such that the electrical signal from the signal generator 50 is routed to only one transducer $10.j$ at any given time. The receiving circuitry is attached to each transducer in parallel with the transmission circuitry. The electrical receiving lines from the 256 transducers 10 are connected through the electrical strip lines 42 to the inputs of 16 16-to-1 analog multiplexers 60.1, ..., 60.16 where they multiplexed to 16 lines. Each of these 16 electrical lines are multiplexed to 1 line via a 16-to-1 analog multiplexer/amplifier 65. The output of this multiplexer 65 is sent to an analog-to-digital converter 68 which is synchronized with the signal from the signal generator 50. The digitized data from the analog-to-digital converter is then stored in a computer 72.

CREATING THE IMAGE

This invention can produce a two-dimensional map of the scattering potential of a medium which is semi-transparent to acoustic waves. The operation of this invention can be divided into two steps: 1) collection of scattered wave information in the form of the coefficients $m_{jk}$ (j, k = 1, ..., N; j$\neq$k); and 2) numerical calculation of the scattering potential S (x). The two operational steps are described in detail here.

The $(N-1)^2 = 255^2$ coefficients $m_{jk}$ (j, k = 1, ..., N; j$\neq$k) are collected by the embodiment in this fashion. A single frequency (500 kHz) sinusoidal electrical signal is sent from the signal generator 50 to transducer 10.1 which transmits this signal as an acoustic wave into the medium 12. The transmitted acoustic wave scatters from the inhomogeneties of medium 12 which are described by S (x) and impinges upon the other N−1 transducers 10.2, ..., 10.256 which transform these acoustic signals into single frequency electrical signals. After a time T = 68 $\mu$sec corresponding to the twice the transit time of the acoustic wave across the diameter 2 $r_o$ of the device, the acoustic signals at each transducer have reached a steady-state condition. At this time, the electrical signals from each transducer are sequentially routed to the analog-to-digital converter 68 as shown on FIG. 4 where they are digitally compared with the signal from the signal generator 50. The phase and amplitude of each receiving transducer 10.2, ..., 10.256 relative to the transmitting transducer 10.1 are recorded in the memory computer of 72 as the N−1 complex coefficients $m_{jk}$ (k=2, ..., 256), respectively. This data collection procedure then continues by routing the 500 kHz electrical signal to transducer 10.2 which now acts as a transmitter of the acoustic wave. After the time T=68 μsec required for the system to reach a steady-state condition, electrical signals sequentially are measured from the transducers 10.1, 10.3, ..., 10.256 as described above in order to collect the 255 complex coefficients $m_{2k}$ (k=1, 3, ..., 256). The measurement procedure continues until each transducer 10.1, ..., 10.N has acted as a transmitter of the acoustic wave. At this point, a complete set of complex coefficients $m_{jk}$ (j, k=1, ..., N; j≠k) has been measured.

The Fourier transform $\overline{S}$ {$k_1^{\alpha\beta}$, $k_2^{\alpha\beta}$} of the scattering potential S (x) is now calculated with the use of equation 8. The right side of equation 8 is comprised of the now measured coefficients $m_{jk}$, the tabulated Hankel functions $H_a(k_o r_o) = H_a(107)$ (a=p, q) ($k_o r_o$ = 107 for this preferred embodiment), and the values $\theta_b = 2\pi b/N$ (b=j, k, α, β). Where the summation of these known quantities over −N/2 < p,q < N/2 and over j,k=1, ..., N (N=256 for this preferred embodiment) for each value of $\theta_\alpha$, $\theta_\beta$ results in the two-dimensional matrix $\overline{S}$ {$k_1^{\alpha\beta}$, $k_2^{\alpha\beta}$}. Finally, the complex scattering potential S (x,y) is calculated by performing an inverse Fourier transform of $\overline{S}$ {$k_1^{\alpha\beta}$, $k_2^{\alpha\beta}$} as shown in equation 10. The scattering potential S (x,y) was shown to be a function of both the sound speed c (x,y) and the density ρ (x,y). The sound speed and the density are highly correlated (c=[Y/ρ]$^{\frac{1}{2}}$ where Y (x,y) is the spatially varying compliance of the medium) so an image of the scattering potential may be sufficient for visual analysis of the medium. However, an alternate embodiment of the invention involves measuring S (x,y) at two frequencies. It is then possible to extract separate maps of the sound speed c (x,y) and the density ρ (x,y).

SOFTWARE

Our computer software can be described by reference FIGS. 7 and 8. FIG. 7 outlines our preprocessing steps to preprocess the wave data prior to processing the data for the image.

Step 1 allows us to deal with dead channels.

Step 2 cancels systematic electrical noise.

Step 3 eliminates most transmitter receiver cross-talk.

Step 4 normalized receiver data.

Step 5 normalizes the signal data to the background data.

Step 6 is our preferred optional approach for imaging most objects we have experimented with, especially larger objects.

Steps 7, 8 and 9 are other options we have tried to achieve better images under different conditions.

Figure 8:
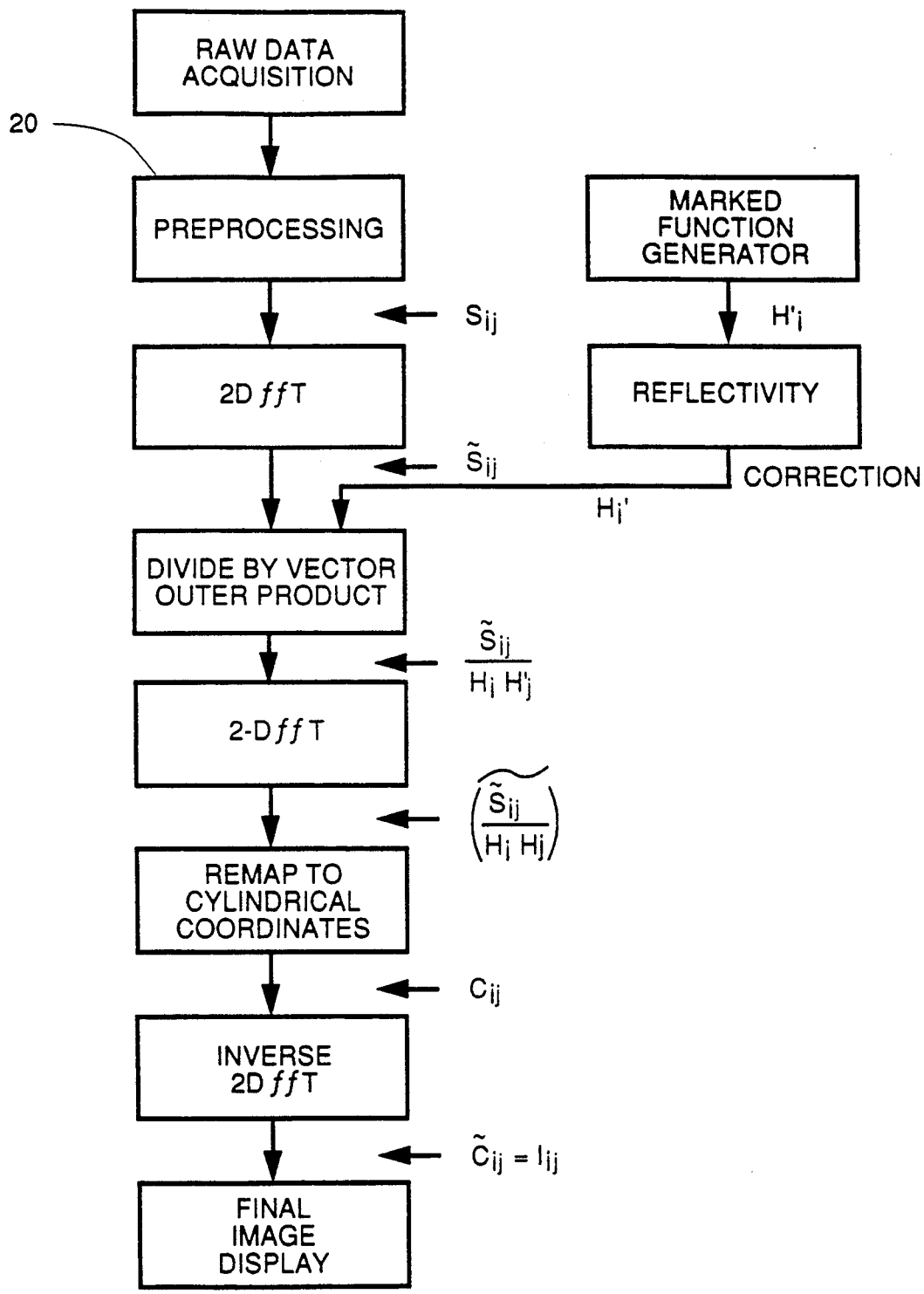
FIG. 8 is a computer flow chart of our reconstruction method.

FIG. 8 is a flow diagram describing the process of producing the image. Note, the preprocessing steps of FIG. 7 are represented by the "reprocessing" box 20.

COMPUTER SIMULATION

A computer simulation of the system was developed to test the reconstruction technique. This simulation uses numerical finite element analysis to propagate acoustic waves into a hypothetical scattering medium with a predetermined scattering potential $S_{test}(x)$. A single frequency acoustic wave, propagated from each transmitter, is numerically scattered from the medium 12 by numerically solving equation 3 for the boundary conditions displayed in FIG. 1. The simulation then records the complex amplitudes $m_{jk}$ at the receivers. The reconstruction algorithm computes the scattering potential $S_{calc}(x)$ which is then compared to the original scattering potential $S_{test}(x)$. In this way, we were able to test the robustness of the reconstruction algorithm for a variety of scattering media. Initial tests on a $(\lambda/4)^2$ sized object inbedded in a spatial noise distribution demonstrate excellent robustness even with 20% variations in the sound speed.

Figure 9:
FIG. 9 is a composite simulation of a human breast.
Figure 10:
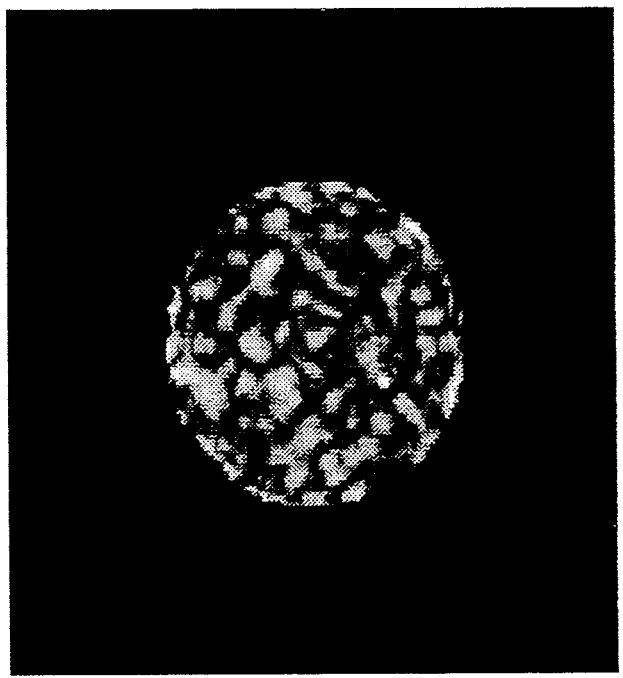
FIG. 10 is a computer reconstructed breast using the mathematical processes according to the present invention.

The results of the simulation are shown in FIGS. 9 and 10. FIG. 9 shows a computer simulated breast. The breast is represented in cross-section by the circular areas in the center of the images. The breast is approximately 4" in diameter. Light and dark variations represent changes in the speed of sound in the breast material. The small spot in the lower right portion of the breast represents a 1/16" inclusion or micro calcification. In FIG. 10 we have reconstructed the scattering potential of the breast material using the mathematical processes discussed above with a presumed 256 transducer element. FIG. 10 clearly shows the inclusion in the lower right portion of the breast.

ACTUAL IMAGES

Figure 11:
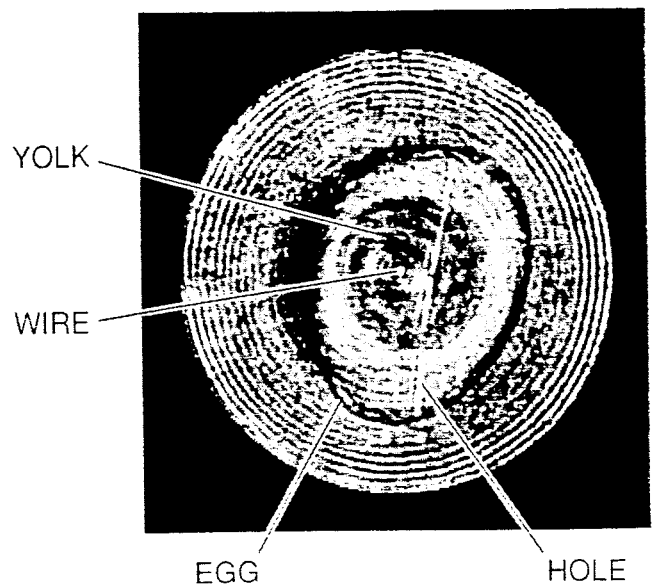
FIG. 11 is an image of a boiled egg produced by the prototype described in FIGS. 1–4.
Figure 12:
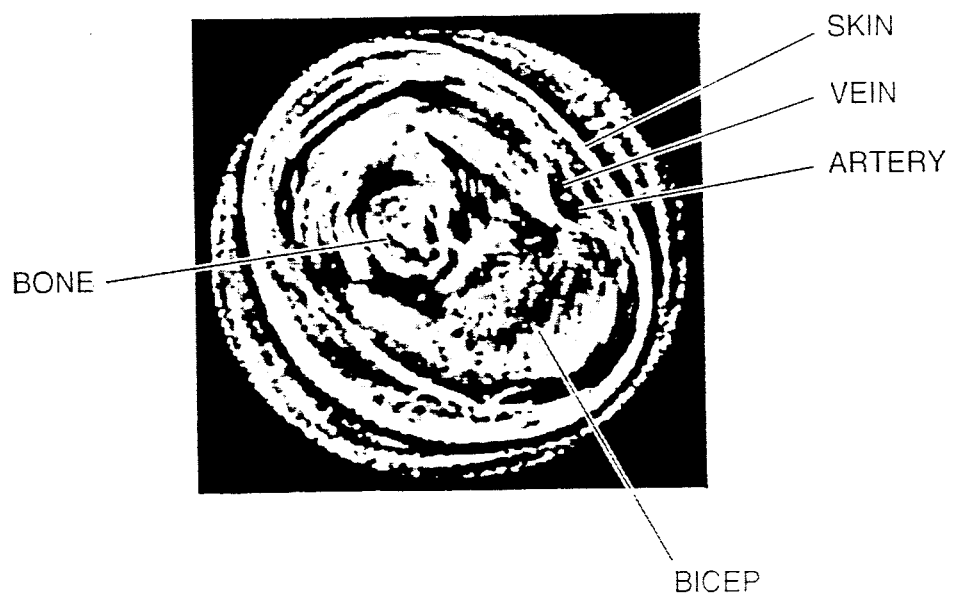
FIG. 12 is an image of the cross section of the upper arm of one of the inventors produced with the prototype device described in FIGS. 1–4.
Figure 13:
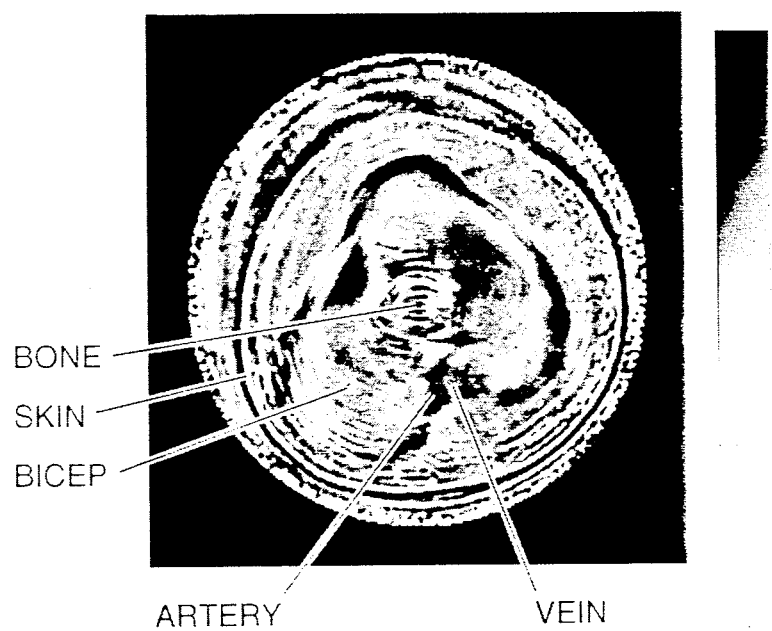
FIG. 13 is an image of the cross section of the upper arm of a female co-worker produced with the prototype device described in FIGS. 1-4.

FIGS. 11, 12 and 13 show actual images obtained using the prototype device above by reference to FIGS. 1-4. FIG. 11 is a tomographic image of a shelled boiled egg. The yolk is easily distinguished. The line is an image of a hole punched through the egg and the spot is a cross-section image of a vertical wire used to hold the egg is place in the device.

FIG. 12 is a tomographic image of the upper arm of one of the Applicants clearly showing muscle, bone blood vessels and skin. FIG. 13 is a tomographic upper arm of a female co-worker of Applicant in the image. Note the larger amount of fat between the muscle and the skin. The images in FIGS. 11, 12 and 13 were produced using by summing data produced at ten frequencies in evenly spaced at 5 kHz interval from 510 kHz to 560 kHz.

ALTERNATE EMBODIMENTS

Figure 5:
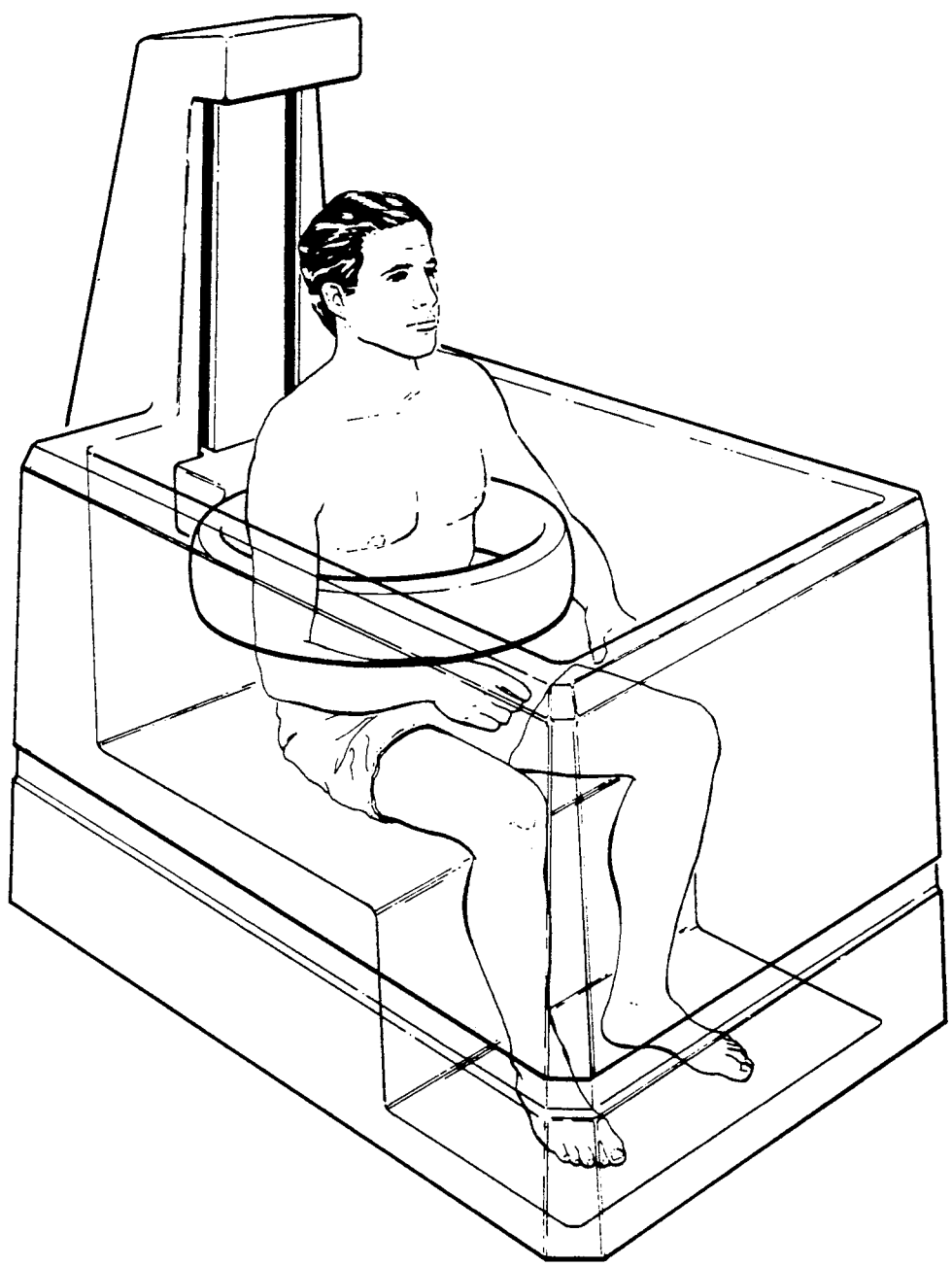
FIG. 5 is an illustration of the invention utilized for abdomen imaging.
Figure 6:
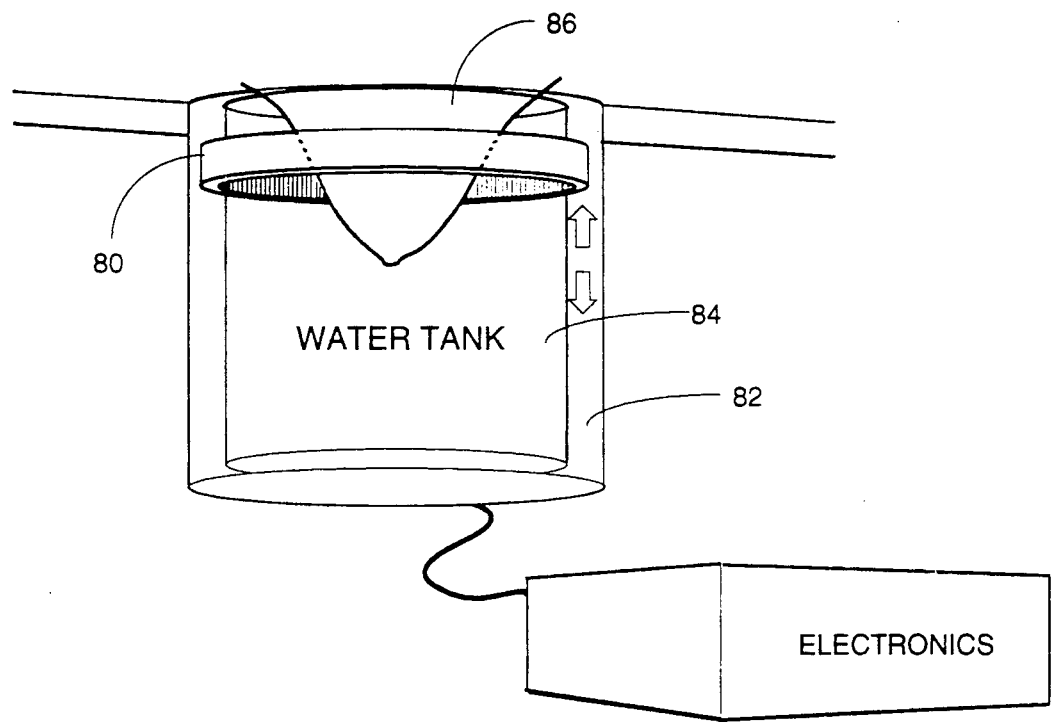
FIG. 6 is an illustration of the invention utilized for breast imaging.

Alternate embodiments of the invention also include the geometry of the transducer array. These alternate embodiments may be appropriate to facilitate coupling of the acoustic waves to various parts of the human body including, for example, the abdomen, female breast, cranial cavity, neck, arm and thigh or to other non-human subjects. An embodiment designed to image the abdomen region of human patients is shown in FIG. 5. A device to perform mammography examination is shown in FIG. 6. In this embodiment the ring of 256 transducers 80 is moveable vertically in an oil tank 82 surrounding water tank 84 so that a complete scan of female breast 86 can be obtained. An embodiment designed to image arteries and veins in arms and legs is shown in FIG. 7. Alternate embodiments include a ring of acoustic transducers which do not lie on the locus of a circle, a ring of transducers which do not completely encircle the medium which is to be imaged, a set of transducers which is in segments of various lengths which partially circumscribe the medium, and a set of transducers arranged in parallel rows on opposite sides of the medium to be imaged. Another embodiment which concerns the use of a rubber fluid-filled bladder to couple the acoustic waves from the transducers to the medium is shown in FIG. 5 and FIG. 7. Various numbers of transducers could be utilized but the number should be at least eight. and as indicated above, transducers should preferably be spaced no more farther apart than one half wavelength of the acoustic wave being transmitted. For non-circular arrays, the algorithm derived above would have to be recalculated to account for the appropriate boundary conditions. Several variations in transducers could be utilized instead of the PZT5A. These include other transducers constructed from piezoelectric zirconate titanate or from piezoelectric film (PVDF), copolymers, or composites of piezoelectric ceramics and polymers (see "Composites Piezoelectric: Basic Research to a Practical Device," W. Smith and A. Shaulov, Ferroelectrics, 10,309 (1988) and references therein).

An alternate embodiment concerns adjustment of the thickness of the tomographic slice which is imaged by the device. This adjustment can be accomplished by means of an aperture which blocks or absorbs sound waves. One embodiment of this aperture shown in FIG. 11 is strips of sound absorbing material (which cover the top and bottom of the transducers except of a small slice in the middle. Another embodiment concerns fabrication of the transducers as shorter in the vertical (#2) direction (see FIG. 3).

We have tested our prototype at frequency in the range of 510 kHz to 560 kHz with good results and we expect that these range could be extended with our technique from 100 kHz to 4 MHz.

Although the preferred embodiment described above uses the same transducers to broadcast and receive, separate means for broadcasting and receiving could be rotated around the medium to simulate a ring of broadcasting transducers. A similar arrangement could be provided to rotate a receiver to simulate a ring of receiving transducers.

Another embodiment is to perform the reconstruction algorithm at multiple frequencies and to reconstruct multiple images. These images are then summed to reinforce the desired reconstruction while suppressing unwanted artifacts such as multiple scattering and reflections. In order to provide good artifact suppression, the frequency separation $\Delta v$ should be $\Delta v < c_o/D$ where $c_o$ is the average sound speed in the medium and D is the radius of the transducer ring, and the total frequency range $v_{tot}$ should be as large as feasible.

The reader should construe the above described embodiments of this invention as example and the scope of this invention shall be determined by the appended claim and their legal equivalents.

What is claimed is:

1. An acoustic imaging device for providing an image of at least a portion of a medium comprising:
    a. an acoustic broadcasting means for broadcasting into said medium an acoustic signal from a plurality of at least seven locations partially surrounding said medium, one location at a time said signal being at least one frequency and continuous for a period of time at least equal to twice the travel time of said acoustic signal across said medium,
    b. an acoustic signal detection means for detecting, at a plurality of closely spaced locations at least partially surrounding said medium, acoustic signals broadcast by said broadcasting means,
    c. a data collection and comparison means for comparing signals broadcast to signals received in order to provide with respect to each of said at least seven locations a set of data representing the phases and amplitudes of acoustic signals received at said at least seven locations relative to the phase and amplitude of the signals broadcast from at least seven locations, and
    d. a computing means including means for effecting a remap algorithm for mathematically constructing an image of at least a portion of said medium utilizing said set of phase and amplitude data.

2. An acoustic imaging device as in claim 1 wherein the locations of said broadcasting means and detection means are in a single plane generally defining an image plane and said constructed image of at least a portion of said medium is an image of a cross section of said medium in said plane.

3. An acoustic imaging device as in claim 2 wherein said computing means comprise a matrix manipulation digital computer programmed to perform inverse Fourier transforms.

4. An acoustic imaging device as in claim 1 wherein said said means for effecting implements said algorithm based on a plane wave expansion of a cylindrical wave.

5. An acoustic image device as in claim 1 wherein said set of data representing said phases and amplitudes is also a two-dimensional matrix representing the Fourier transform of the acoustic scattering potential of the medium.

6. An acoustic imaging device as in claim 1 wherein said broadcasting means comprise at least eight transducers.

7. An acoustic image device as in claim 6 wherein said detection means comprise the same at least eight transducers comprised in said broadcasting means.

8. A device as in claim 7 wherein said transducers are constructed from piezoelectric zirconate titanate, 9. A device as in claim 7 wherein said transducers are constructed from a piezoelectric film (PVDF) or copolymers.

10. A device as in claim 7 wherein the transducers are constructed from a piezoelectric composite.

11. A device as in claim 7 wherein the dimensions of the device and number of transducers and their arrangement and the wavelength of the acoustic signals broadcasted are such that the spacing of the acoustic transducers is less such than half such wavelength of the acoustic signals in the medium.

12. A device as in claim 6, wherein said transducers are arranged in parallel lines on opposite sides of said medium.

13. A device as in claim 1 wherein said broadcasting means comprises a transmitter of acoustic waves which is mechanically rotated to simulate a ring of transmitter locations.

14. An acoustic imaging device as in claim 1 wherein said means for effecting a remap algorithm includes means for providing a plane wave expansion of a spherical wave.

15. A device as in claim 1 wherein said at least one frequency is a plurality of frequencies and said computing means includes means for using said plurality of frequencies detected by said detection means for the mathematical construction of the image.

* * * * *